(12) United States Patent
Smith et al.

(10) Patent No.: US 6,682,908 B1
(45) Date of Patent: Jan. 27, 2004

(54) MOUSE GROWTH HORMONE SECRETAGOGUE RECEPTOR

(75) Inventors: Roy G. Smith, Houston, TX (US); Leonardus H. T. Van der Ploeg, Scotch Plains, NJ (US); Andrew D. Howard, Park Ridge, NJ (US); Hui Zheng, Houston, TX (US); Karen Kulju McKee, Middletown, NJ (US); Michael M. Jiang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/743,475

(22) PCT Filed: Jul. 8, 1999

(86) PCT No.: PCT/US99/15375
§ 371 (c)(1),
(2), (4) Date: Jun. 13, 2001

(87) PCT Pub. No.: WO00/02918
PCT Pub. Date: Jan. 20, 2000

Related U.S. Application Data

(60) Provisional application No. 60/092,361, filed on Jul. 10, 1998.

(51) Int. Cl.$^7$ .............. C12N 5/10; C12N 5/16; C12N 15/12; C12P 21/02; C07K 14/47
(52) U.S. Cl. .......... 435/69.1; 435/71.1; 435/320.1; 435/471; 435/252.3; 435/325; 530/351; 536/23.5
(58) Field of Search .......... 435/69.1, 71.1, 435/320.1, 471, 252.3, 325; 530/351; 536/23.5

(56) References Cited

U.S. PATENT DOCUMENTS

| | | |
|---|---|---|
| 3,239,345 A | 3/1966 | Hodge et al. |
| 4,036,979 A | 7/1977 | Asato |
| 4,410,513 A | 10/1983 | Momany |
| 4,411,890 A | 10/1983 | Momany |
| 5,057,417 A | 10/1991 | Hammonds et al. |
| 5,206,235 A | 4/1993 | Fisher et al. |
| 5,283,241 A | 2/1994 | Bochis et al. |
| 5,284,841 A | 2/1994 | Chu et al. |
| 5,310,737 A | 5/1994 | Fisher et al. |
| 5,317,017 A | 5/1994 | Ok et al. |
| 5,374,721 A | 12/1994 | Schoen et al. |
| 5,430,144 A | 7/1995 | Schoen et al. |
| 5,434,261 A | 7/1995 | Schoen et al. |
| 5,438,136 A | 8/1995 | Devita et al. |
| 5,492,916 A | 2/1996 | Morriello et al. |
| 5,492,920 A | 2/1996 | Chen et al. |
| 5,494,919 A | 2/1996 | Morriello et al. |
| 5,583,010 A | 12/1996 | Baumbach et al. |
| 5,591,641 A | 1/1997 | Thorner et al. |
| 5,830,433 A | 11/1998 | Dean et al. |

FOREIGN PATENT DOCUMENTS

| | | |
|---|---|---|
| EP | 0 144 230 | 3/1984 |
| EP | 0 513 974 | 12/1992 |
| WO | WO 89/07110 | 8/1989 |
| WO | WO 89/07111 | 8/1989 |
| WO | WO 93/04081 | 3/1993 |
| WO | WO 94/07486 | 4/1994 |
| WO | WO 94/08583 | 4/1994 |
| WO | WO 94/11012 | 5/1994 |
| WO | WO 94/13696 | 6/1994 |
| WO | WO 94/19367 | 9/1994 |
| WO | WO 95/03289 | 2/1995 |
| WO | WO 95/03290 | 2/1995 |
| WO | WO 95/09633 | 4/1995 |
| WO | WO 95/11029 | 4/1995 |
| WO | WO 95/12598 | 5/1995 |
| WO | WO 95/13069 | 5/1995 |
| WO | WO 95/14666 | 6/1995 |
| WO | WO 95/16675 | 6/1995 |
| WO | WO 95/16692 | 6/1995 |
| WO | WO 95/17422 | 6/1995 |
| WO | WO 95/17423 | 6/1995 |
| WO | WO 95/34311 | 12/1995 |
| WO | WO 96/02530 | 2/1996 |
| WO | WO 97/22004 | 6/1997 |
| WO | WO 98/14780 | 4/1998 |

OTHER PUBLICATIONS

Howard, A. et al. "A Receptor in Pituitary and Hypothalamus That Functions in Growth Hormone Release", Science, 1996, vol. 273, pp. 974–977.

Aloi, J. et al. "Neuroendocrine Responses to a Novel Growth Hormone Secretagogue, L–692,429, in Healthy Older Subjects", Journal of Clinical Endocrinology and Metabolism, 1994, vol. 79, pp. 943–949.

Bowers, C. "Editorial: On a Peptidomimetic Growth Hormone–Releasing Peptide", Journal of Clinical Endocrinology and Metabolism, 1994, vol. 79, pp. 940–942.

Sethumadhavan, K. et al. "Demonstration and Characterization of the Specific Binding of Growth Hormone–Releasing Peptide to Rat Anterior Pituitary and Hypothalamic Membranes", Biochemical and Biophysical Research Communications, 1991, vol. 178, pp. 31–37.

(List continued on next page.)

*Primary Examiner*—Gary Kunz
*Assistant Examiner*—Fozia Hamud
(74) *Attorney, Agent, or Firm*—Joanne M. Giesser; Anna L. Cocuzzo; Patricia Chisholm

(57) ABSTRACT

A mouse growth hormone secretagogue receptor has been isolated, cloned and sequenced. This receptor is characteristic of the G-protein family of receptors. Mouse growth hormone secretagogue receptors may be used to screen and identify compoumds which bind to the mouse growth hormone secretagogue receptor. Such compounds may be used in the treatment of conditions which occur when there is a shortage of growth hormone, such as observed in growth hormone deficient children, elderly patients with musculoskeletal impairment and those recovering from hip fracture and osteoporosis. Targeted disruption of the mouse GHS-R gene may prove useful in elucidation of the mechanism of action and role of the growth hormone secretagogues in human and animal physiology.

12 Claims, 7 Drawing Sheets-

OTHER PUBLICATIONS

Pomes, A. et al. "Solubilization and Characterization of a Growth Hormone Secretagogue Receptor from Porcine Anterior Pituitary Membranes", Biochemical and Biophysical Research Communications, 1996, vol. 225, pp. 939–945.

Guan, X. et al. "Distribution of mRNA encoding the growth hormone secretagogue receptor in brain and peripheral tissues", Molecular Brain Reserach, 1997, vol. 48, pp. 23–29.

Pong, S. et al. "Identification of A New G–Protein–Linked Receptor for Growth Hormone Secretagogues", Molecular Endocrinology, 1996, vol. 10, pp. 57–61.

McKee, K. et al., Database Genbank, Accession No. 055040, 1998.

Tan, C. et al., Database Genbank, Accession No. 043664, 1998.

McKee, K. et al., Database Genbank, Accession No. AF044602, 1998.

Tan, C. et al., Database Genbank, Accession No. AF044600, 1999.

Adams, E. et al. "Presence of Growth Hormone Secretagogue Receptor Messenger Ribonucleic Acid in Human Pituitary Tumors and Rat GH3 Cells", Journal of Clinical Endocrinology and Metabolism, 1998, vol. 83, pp. 638–642.

Howard, A. et al. "Molecular Analysis of the Growth Hormone Secretagogue Receptor", Growth Hormone Secretagogues, 1999, pp. 35–51.

McKee, K. et al. "Cloning and Characterization of Two Human G Protein–Coupled Receptor Genes (GPR38 and GPR39) Related to the Growth Hormone Secretagogue and Neurotensin Receptors", Genomics, 1997, vol. 46, pp. 426–434.

Feighner, S. et al. "Receptor for Motilin Identified in the Human Gastrointestinal System", Science, 1999, vol. 284, pp. 2184–2188.

Cheng, K. et al. "Evidence for a Role of Protein Kinase–C in His–D–Trp–Ala–Trp–D–Phe–Lys–NH2–Induced Growth Hormone Release from Rat Primary Pituitary Cells", Endocrinology, 1991, vol. 129, pp. 3337–3342.

McKee, K. et al. "Molecular Analysis of Rat Pituitary and Hypothalamic Growth Hormone Secretagogue Receptors", Molecular Endocrinology, 1997, vol. 11, pp. 415–423.

Bennett, P. et al. "Hypothalamic Growth Hormone Secretagogue–Receptor (GHS–R) Expression Is Regulated by Growth Hormone in the Rat", Endocrinology, 1997, vol. 138, pp. 4552–4557.

Soldati, T. et al. "Alternative Ribosomal Initiation Gives Rise to Chicken Brain–type Creatine Kinase Isoproteins with Heterogeneous Amino Termini", the Journal of Biological Chemistry, 1990, vol. 265, pp. 4498–4506.

Kozak, M. et al. "Compilation and analysis of sequences upstream from the translational start site in eukaryotic mRNAs", Nucleic Acids Research, 1984, vol. 12, pp. 857–872.

Button, D. et al. "Aequorin–expressing mammalian cell lines used to report Ca2+ mobilization", Cell Calcium, 1993, vol. 14, pp. 663–671.

Kao, J. et al. "Photochemically Generated Cytosolic Calcium Pulses and Their Detection by Fluo–3", The Journal of Biological Chemistry, 1989, vol. 264, pp. 8179–8184.

Zlokarnik, G. et al. "Quantitation of Transcription and Clonal Selection of Single Living Cells with beta–Lactamase as Reporter", Science, 1998, vol. 279, pp. 84–88.

Ok, D. et al. "Structure–Activity Relationships of the Non–Peptidyl Growth Hormone Secretagogue L–692–429", Bioorganic & Medicinal Chemistry Letters, 1994, vol. 4, pp. 2709–2714.

Patchett, A. et al. "Design and biological activities of L–163,191 (MK–0677): A potent, orally active growth hormone secretagogue", Proc. Natl. Acad. Sci. USA, 1995, vol. 92, pp. 7001–7005.

Schoen, W. et al. "Growth Hormone Secretagogues", Annual Reports in Medicinal Chemistry, 1993, vol. 28, pp. 177–186.

Smith, R. et al. "A nonpeptidyl Growth Hormone Secretagogue", Science, 1993, vol. 260, pp. 1640–1643.

King, K. et al. "Control of Yeast Mating Signal Transduction by a Mammalian B2–Adrenergic Receptor and Gs a Subunit", Science, 1990, vol. 250, pp. 121–123.

Julius, D. et al. "Molecular Characterization of a Functional cDNA Encoding the Serotonin 1c Receptor", Science, 1988, vol. 241, pp. 558–564.

Cubitt, A. et al. "Understanding, improving and using green fluorescent proteins", TIBS, 1995, vol. 20, pp. 448–455.

Feighner, S. et al. "Structural Requirements for the Activation of the Human Growth Hormone Secretagogue Receptor by Peptide and Nonpeptide Secretagogues", Molecular Endocrinology, 1998, vol. 12, pp. 137–145.

Williams, R. "Textbook of Endocrinology, Fifth Edition" 1974, pp. 790–791.

Wu, D. et al. "Activation of Phospholipase C by al–Adrenergic Receptors Is Mediated by the a Subunits of Gq Family", The Journal of Biological Chemistry, 1992, vol. 267, pp. 25798–25802.

Ganong, W. "Review of Medical Physiology, seventeenth edition", pp. 373–374, 1995.

DNA sequence of mouse GHS-R.
Lambda vector, 5' and 3' untranslated sequence and intron are shown in lower case.
Translated sequence is shown in upper case.

AA
agagaggagccctcacacactcgctttgcagcgcctgccttccgcaagagcccacgcactcggacgcttgtggggagcacgac
aggcttgctggggcgagatctccagtgccaggcaactgctggtggcgccgccgtttgagtgacaggtaagtgagtgcgtgaca
gtcgaggctgtattgggagaccgggactgtgtggggaagatagtgggaaggggggaagaaaagagagagatgtgggagggag
gggagaggaggaacggaaggaaataggggagagacgtgcagtgggtcactctcttcctttcatcgctaatgttcgcaccccattc
caccttctcctaggcttcttctcacttctctcttccccaagcatccttcctgctgctcgcgcccattcctcccccacgccgccccccgc
ccggcccccactcttccgcgcctaggaggacctcctcaggggaccagatttccgcgcggctgcgaccccaagcctggcaacA
TGTGGAACGCGACGCCCAGCGAGGAGCCGGAGCCTAACGTCACGCTGGAC
CTGGACTGGGACGCTTCTCCCGGCAACGACTCACTCTCTGACGAACTGCTG
CCACTGTTCCCCGCGCCGCTGCTGGCGGGCGTCACTGCCACCTGCGTGGC
GCTCTTCGTGGTGGGCATCTCGGGCAACCTGCTCACCATGCTGGTGGTGTC
CCGCTTCCGCGAGCTGCGCACCACCACCAACCTCTACCTATCCAGCATGGC
CTTCTCCGATCTGCTCATCTTCCTGTGCATGCCGCTGGACCTCGTCCGCCTC
TGGCAGTATCGGCCCTGGAACTTCGGCGACCTGCTCTGCAAACTCTTCCAG
TTTGTCAGCGAGAGCTGCACCTACGCCACGGTCCTCACCATCACCGCGCTG
AGCGTCGAGCGCTACTTCGCCATCTGCTTCCCGCTGCGGGCCAAGGTGGTG
GTCACCAAGGGCCGTGTGAAGCTGGTCATCCTTGTCATCTGGGCCGTGGCC
TTCTGCAGCGCGGGGCCCATCTTCGTGCTGGTGGGCGTGGAGCACGAGAA
CGGCACAGATCCCCGGGACACCAACGAGTGCCGCGCCACCGAGTTCGCTG
TGCGCTCTGGGCTGCTCACCGTCATGGTGTGGGTGTCCAGCGTCTTCTTCTT
TCTACCGGTCTTCTGCCTCACTGTGCTCTACAGTCTCATCGGGAGGAAGCTA
TGGCGGAGACGCGGCGATGCAGCGGTGGGCGCCTCGCTCCGGGACCAGA
ACCACAAACAGACAGTGAAGATGCTTGgtgagttctgacaccccggtggctttcttcccccactgcttg
ctctttgccagagccctctatttctgtttctggtcgtctccatctctccctaagtctctcaagtctctgtctgtctctgyctctctsttggttctt
ggtctcactgcttckggttttttttcctctgtctgtccctgtatcttctccacgaaaaagcccctcatattggcaattccctaaatgagtact
ggtctgggaaatttggtccaagatggaaatacctcattatggtttattgagtccctaattgttaayggtkymkcwymtwgwct
cacatagaatttgtggttatcmaagtmataatattaaggtaagcaggcaggyawtgggtttagaaatyrctccatggtaartctaa
ccamaaawttgggtcactctgttaargaygryttatagatgtrtttgtttgtttkcaatattrggattttrttytctgccctgcmyctkyc
tcagataattacatccactcttgtttagtctatggttttgccaggaggggcttcatgctggggtctcctttttcttgttttgtatttgtctccc
cagtaatataggccaggatagggtggagaagtcatccttcctcaaactgtccttcaggaaggtctgggtactgaacggttactgca
taaactctgcttccccaaaggcatgtgcttggtgtggtaaagtcatgaagatggtgctcatgtccaagaggaacctctgatctcacttt
tcaagggatttcatgtttgctgacattaatacttgttagttttgcagggggatgatttctcattgcaatttattattctcaaattctgcatgt
cagaatgttagagatttctcagggatgtcaggttctgtttccagatgagtgattgccctgtgtcctccattggactgtaaactcatatgc
accagacagggtctacattgctgccgtggtgcatagccttccatgtgtcacttagtcctaaagagaagttactaataacctaatctcac
taatctcactggcatctcaatgccgatccattgtcatctgaaaatttgaaggggacattaaagtggcacagggaccagaacaatatt
tttctctcattgctgaattttaaaaacaatctaaaaaattggaattcttgaagaaactatcttatatgactaaaatgaagccttgggtgggt
gctaattattattgtctggcttacctgcccccccccactactatatcttttagagatgacacagacttgctttccctgtggctactaatccca
attgcacattcagtcccttgatagacttactctaaaaaatctaagttcagcggtccacgaaacataacaaagcctgtcctaaaacagaaa
gaaagaaagaaagaaagaaagaaagaaagaaagaaagaaagaaagaaagaaaacagaagacaaacaaggtctttccccattc
cctaacatacaggaatggaaattattaagtctacgtgatagccaatgaatctgtttcttaagtatgcccacaagggtgctgccggagc
cattgctcagggctggagtatttactgggcatgcttgacccagcatggagggtgagaagtgctcctgggaactctgatccactgc
tgtggtggagagcaaacacctggcctcatttatacttgttgtctgtataatgcatataaatggaggataatcattaatgaactgtttagtt
gggtcatcatgccaagtcagtcacaaagccaagtcgttatcacatagaaagactgggaagcccagtggagattgttagctgttggt
ctgacagtctcactgtgtgctatctatagtgttagaacggatggaggcagtatttatgtgaagagcagggtgtcgtgtttcctgtgtca
aagagcaagatgtgatgtttgtcagtgggcatgcccctcatggagaaaagagatccggacttaaaaatgtgaagtgatttatgcc
gtgtcacacccatgctccaccctgatggtctctctttgtgtgccttcagCTGTGGTGGTGTTTGCTTTCATCC
TCTGCTGGCTGCCCTTCCACGTGGGAAGATATCTGTTTTCCAAGTCTTTCGA
GCCTGGCTCTCTGGAGATCGCGCAGATCAGTCAGTACTGCAACCTGGTGTC
CTTTGTCCTCTTCTACCTCAGCGCTGCCATCAACCCCATTCTGTACAACATCA

FIG.1A

TGTCCAAGAAGTACCGGGTGGCCGTGTTCAAACTTCTAGGATTTGAATCCTT
CTCCCAGAGAAAGCTTTCCACTCTGAAGGATGAGAGTTCCCGGGCCTGGAC
AAAGTCGAGCATCAATACATGAcatcgcagcgcatctctccgtcatcgctcattgctccacaccagaagcca
tagccaagcgggacttggggaggaggcagaacgtcagtttggggattagagacaaatggatctggaaacaattgggggtgggg
agtagagccagatgggcagggtccgtgcagattgatctatttgtgcgcccaccagagcactcatgtgcagcccctgcacacctgt
gtctgtgattttgcgaatttgcatttggagcttctgacagctttgcagctcgaaggagggaggggcgcagagcaggcaacggcc
gtccttcttggtgtgtaacactaaactccatttgcttttctcatcataatag

FIG.1B

ATGTGGAACGCGACGCCCAGCGAGGAGCCGGAGCCTAACGTCACGCTGGA
CCTGGACTGGGACGCTTCTCCCGGCAACGACTCACTCTCTGACGAACTGCT
GCCACTGTTCCCCGCGCCGCTGCTGGCGGGCGTCACTGCCACCTGCGTGG
CGCTCTTCGTGGTGGGCATCTCGGGCAACCTGCTCACCATGCTGGTGGTGT
CCCGCTTCCGCGAGCTGCGCACCACCACCAACCTCTACCTATCCAGCATGG
CCTTCTCCGATCTGCTCATCTTCCTGTGCATGCCGCTGGACCTCGTCCGCCT
CTGGCAGTATCGGCCCTGGAACTTCGGCGACCTGCTCTGCAAACTCTTCCA
GTTTGTCAGCGAGAGCTGCACCTACGCCACGGTCCTCACCATCACCGCGCT
GAGCGTCGAGCGCTACTTCGCCATCTGCTTCCCGCTGCGGGCCAAGGTGGT
GGTCACCAAGGGCCGTGTGAAGCTGGTCATCCTTGTCATCTGGGCCGTGGC
CTTCTGCAGCGCGGGGCCCATCTTCGTGCTGGTGGGCGTGGAGCACGAGA
ACGGCACAGATCCCCGGGACACCAACGAGTGCCGCGCCACCGAGTTCGCT
GTGCGCTCTGGGCTGCTCACCGTGATGGTATGGGTGTCGAGCGTCTTCTTC
TTTCTGCCGGTCTTCTGCCTCACTGTGCTCTACAGTCTCATCGGGAGGAAGC
TGTGGCGGAGGCGCGGCGACGCGGCGGTGGGCTCCTCGCTCAGGGACCA
GAACCACAAACAGACAGTGAAGATGCTTGCTGTGGTGGTGTTTGCTTTCATC
CTCTGCTGGCTGCCCTTCCACGTGGGAAGATATCTGTTTTCCAAGTCTTTCG
AGCCTGGCTCTCTGGAGATCGCGCAGATCAGTCAGTACTGCAACCTGGTGT
CCTTTGTCCTCTTCTACCTCAGCGCTGCCATCAACCCCATTCTCTACAACATC
ATGTCCAAGAAGTACCGGGTGGCCGTGTTCAAACTTCTAGGATTTGAATCCT
TCTCCCAGAGAAAGCTTTCCACTCTGAAGGATGAGAGTTCCCGGGCCTGGA
CAAAGTCGAGCATCAATACATGA

FIG.2

Translate DNA Sequence m GHRS Ia(1,1095)
With Standard Genetic Code

Molecular Weight 40973.00 Daltons
    364 Amino Acids
    34 Strongly Basic(+) Amino Acids (K,R)
    28 Strongly Acidic(-) Amino Acids (D,E)
    165 Hydrophobic Amino Acids (A,I,L,F,W,V)
    95 Polar Amino Acids (N,C,Q,S,T,Y)

8.445 Isolectric Point
    6.125 Charge at PH 7.0

Total number of bases translated is 1095
    % A = 16.62        [182]
    % G = 27.95        [306]
    % T = 23.01        [252]
    % C = 32.42        [355]
    % Ambiguous = 0.00    [0]

% A+T = 39.63      [434]
    % C+G = 60.37      [661]

Davis,Botstein,Roth Melting Temp C. 89.19
    Wallace Temp C        4222.00

Codon usage:

| Codon | AA | # | Codon | AA | # | Codon | AA | # | Codon | AA | # |
|---|---|---|---|---|---|---|---|---|---|---|---|
| gca | Ala(A) | 0 | cag | Gln(Q) | 7 | uug | Leu(L) | 0 | uaa | Ter(.) | 0 |
| gcc | Ala(A) | 11 | --- | Gln(Q) | 7 | --- | Leu(L) | 51 | uag | Ter(.) | 0 |
| gcg | Ala(A) | 9 | gaa | Glu(E) | 2 | aaa | Lys(K) | 3 | uga | Ter(.) | 1 |
| gcu | Ala(A) | 5 | gag | Glu(E) | 13 | aag | Lys(K) | 11 | --- | Ter(.) | 1 |
| --- | Ala(A) | 25 | --- | Glu(E) | 15 | --- | Lys(K) | 14 | aca | Thr(T) | 4 |
| aga | Arg(R) | 2 | gga | Gly(G) | 2 | aug | Met(M) | 7 | acc | Thr(T) | 12 |
| agg | Arg(R) | 3 | ggc | Gly(G) | 11 | --- | Met(M) | 7 | acg | Thr(T) | 3 |
| cga | Arg(R) | 0 | ggg | Gly(G) | 3 | uuc | Phe(F) | 21 | acu | Thr(T) | 3 |
| cgc | Arg(R) | 8 | ggu | Gly(G) | 0 | uuu | Phe(F) | 6 | --- | Thr(T) | 22 |
| cgg | Arg(R) | 6 | --- | Gly(G) | 16 | --- | Phe(F) | 27 | ugg | Trp(W) | 9 |
| cgu | Arg(R) | 1 | cac | His(H) | 3 | cca | Pro(P) | 1 | --- | Trp(W) | 9 |
| --- | Arg(R) | 20 | cau | His(H) | 0 | ccc | Pro(P) | 8 | uac | Tyr(Y) | 8 |
| aac | Asn(N) | 12 | --- | His(H) | 3 | ccg | Pro(P) | 5 | uau | Tyr(Y) | 2 |
| aau | Asn(N) | 1 | aua | Ile(I) | 0 | ccu | Pro(P) | 2 | --- | Tyr(Y) | 10 |
| --- | Asn(N) | 13 | auc | Ile(I) | 14 | --- | Pro(P) | 16 | gua | Val(V) | 1 |
| gac | Asp(D) | 10 | auu | Ile(I) | 1 | agc | Ser(S) | 9 | guc | Val(V) | 12 |
| gau | Asp(D) | 3 | --- | Ile(I) | 15 | agu | Ser(S) | 3 | gug | Val(V) | 25 |
| --- | Asp(D) | 13 | cua | Leu(L) | 2 | uca | Ser(S) | 1 | guu | Val(V) | 0 |
| ugc | Cys(C) | 10 | cuc | Leu(L) | 19 | ucc | Ser(S) | 11 | --- | Val(V) | 38 |
| ugu | Cys(C) | 0 | cug | Leu(L) | 26 | ucg | Ser(S) | 4 | nnn | ???(X) | 0 |
| --- | Cys(C) | 10 | cuu | Leu(L) | 4 | ucu | Ser(S) | 5 | TOTAL | | 365 |
| caa | Gln(Q) | 0 | uua | Leu(L) | 0 | --- | Ser(S) | 33 | | | |

FIG.3A

AA
MWNATPSEEPEPNVTLDLDWDASPGNDSLSDELLPLFPAPLLAGVTATCVALFV
VGISGNLLTMLVVSRFRELRTTTNLYLSSMAFSDLLIFLCMPLDLVRLWQYRPW
NFGDLLCKLFQFVSESCTYATVLTITALSVERYFAICFPLRAKVVVTKGRVKLVI
LVIWAVAFCSAGPIFVLVGVEHENGTDPRDTNECRATEFAVRSGLLTVMVWVS
SVFFFLPVFCLTVLYSLIGRKLWRRRGDAAVGSSLRDQNHKQTVKMLAVVVFA
FILCWLPFHVGRYLFSKSFEPGSLEIAQISQYCNLVSFVLFYLSAAINPILYNIMS
KKYRVAVFKLLGFESFSQRKLSTLKDESSRAWTKSSINT.

FIG.3B

```
huGHS-R      1  MWNATPSEEPGFNLTLADLDWDASPGNDSLGDE   33
ratGHS-R     1  MWNATPSEEPEPNVTL-DLDWDASPGNDSLPDE   32
swGHS-R      1  MWNATPSEEPGPNLTLPDLGWDAPPENDSLVEE   33
mouseGHS-R   1  MWNATPSEEPEPNVTL-DLDWDASPGNDSLSDE   32 huGHS-R      34 LLQLFPAPLLAGVTATCVALFVVGIAGNLLTML   65
ratGHS-R     33 LLPLFPAPLLAGVTATCVALFVVGISGNLLTML   65
swGHS-R      34 LLPLFPTPLLAGVTATCVALFVVGIAGNLLTML   66
mouseGHS-R   33 LLPLFPAPLLAGVTATCVALFVVGISGNLLTML   65 huGHS-R      67 VVSRFRELRTTTNLYLSSMAFSDLLIFLCMPLD   99
ratGHS-R     66 VVSRFRELRTTTNLYLSSMAFSDLLIFLCMPLD   98
swGHS-R      67 VVSRFREMRTTTNLYLSSMAFSDLLIFLCMPLD   99
mouseGHS-R   66 VVSRFRELRTTTNLYLSSMAFSDLLIFLCMPLD   98 huGHS-R     100 LVRLWQYRPWNFGDLLCKLFQFVSESCTYATVL  132
ratGHS-R     99 LVRLWQYRPWNFGDLLCKLFQFVSESCTYATVL  131
swGHS-R     100 LFRLWQYRPWNLGNLLCKLFQFVSESCTYATVL  132
mouseGHS-R   99 LVRLWQYRPWNFGDLLCKLFQFVSESCTYATVL  131 huGHS-R     133 TITALSVERYFAICFPLRAKVVVTKGRVKLVIF  165
ratGHS-R    132 TITALSVERYFAICFPLRAKVVVTKGRVKLVIL  164
swGHS-R     133 TITALSVERYFAICFPLRAKVVVTKGRVKLVIL  165
mouseGHS-R  132 TITALSVERYFAICFPLRAKVVVTKGRVKLVIL  164 huGHS-R     166 VIWAVAFCSAGPIFVLVGVEHEHGTDPWDTNEC  198
ratGHS-R    165 VIWAVAFCSAGPIFVLVGVEHEHGTDPRDTNEC  197
swGHS-R     166 VIWAVAFCSAGPIFVLVGVEHDHGTDPRDTNEC  198
mouseGHS-R  165 VIWAVAFCSAGPIFVLVGVEHEHGTDPRDTNEC  197 huGHS-R     199 RPTEFAVRSGLLTVMVWVSSIFFFLPVFCLTVL  231
ratGHS-R    198 RATEFAVRSGLLTVMVWVSSVFFFLPVFCLTVL  230
swGHS-R     199 RATEFAVRSGLLTVMVWVSSVFFFLPVFCLTVL  231
mouseGHS-R  198 RATEFAVRSGLLTVMVWVSSVFFFLPVFCLTVL  230 huGHS-R     232 YSLIGRKLWRRRRGDAVVGASLRDQNHKQTVKM  264
ratGHS-R    231 YSLIGRKLWRRR-GDAAVGASLRDQNHKQTVKM  262
swGHS-R     232 YSLIGRKLWRRKRGEAAVGSSLRDQNHKQTVKM  264
mouseGHS-R  231 YSLIGRKLWRRR-GDAAVGSSLRDQNHKQTVKM  262
```

FIG.4A

```
huGHS-R     265  LAVVVFAFILCWLPFHVGRYLFSKSFEPGSLEI  297
ratGHS-R    263  LAVVVFAFILCWLPFHVGRYLFSKSFEPGSLEI  295
swGHS-R     265  LAVVVFAFILCWLPFHVGRYLFSKSLEPGSVEI  297
mouseGHS-R  263  LAVVVFAFILCWLPFHVGRYLFSKSFEPGSLEI  295 huGHS-R     298  AQISQYCNLVSFVLFYLSAAINPILYNIMSKKY  330
ratGHS-R    296  AQISQYCNLVSFVLFYLSAAINPILYNIMSKKY  328
swGHS-R     298  AQISQYCNLVSFVLFYLSAAINPILYNIMSKKY  330
mouseGHS-R  296  AQISQYCNLVSFVLFYLSAAINPILYNIMSKKY  328 huGHS-R     331  RVAVFRLLGFEPFSQRKLSTLKDESSRAWTESS  363
ratGHS-R    329  RVAVFKLLGFESFSQRKLSTLKDESSRAWTKSS  361
swGHS-R     331  RVAVFKLLGFEPFSQRKLSTLKDESSRAWTESS  363
mouseGHS-R  329  RVAVFKLLGFESFSQRKLSTLKDESSRAWTKSS  361 huGHS-R     364  INT- -                              366
ratGHS-R    362  INT                                 364
swGHS-R     364  INT-                                366
mouseGHS-R  362  INT- -                              364
```

FIG.4B

MOUSE GROWTH HORMONE SECRETAGOGUE RECEPTOR

This Application is a 371 of PCT/US99/153751 filed on Jul. 8, 1999, which claims benefit of U.S. Provisional Application No. 60/092,361 filed on Jul. 10, 1998.

FIELD OF THE INVENTION

This invention relates to a newly identified receptor, the mouse growth hormone secretagogue receptor (mGHS-R), nucleic acids encoding this receptor; and to the use of a mGHS-R to identify growth hormone secretagogues and compounds that modulate mGHS-R function.

BACKGROUND OF THE INVENTION

Growth hormone secretagogues (GHSs) and secretagogue-like compounds, both peptide and non-peptide, bind to and exert their biological effects (i.e., release of growth hormone (GH)) through a G protein-coupled receptor (GPC-R) distinct from the receptors for growth hormone releasing hormone (GHRH) and somatostatin (SST) (Pong et al., 1996 *Mol. Endocrin.* 10:57–61). The molecular cloning of this growth hormone secretagogue receptor (GHS-R) capitalized on the pivotal observation that GHSs transduce their signal through activation of the phospholipase C pathway (Cheng et al., 1991 *Endocrinology* 129:3337–3342; Howard et al., 1996 *Science* 273:974–977). cDNA and genomic DNA cloning from human, swine, and rat showed that the GHS-R is a protein of 364/366 amino acids containing 7 putative alpha-helical transmembrane (TM) domains, a signature feature of GPC-Rs (Howard et al. 1996; McKee et al., 1997 *Mol. Endocrin.* 11:415–423). In all species evaluated, the GHS-R is encoded by a single highly-conserved gene containing one intron, placed at the C-terminal end of TM domain 5.

The biology of the growth hormone secretagogues (GHSs) is still in a relatively early stage of development. Research is focused on identification of the GHS natural ligand system and understanding the role of the GHS-R in brain regions (substantia nigra, dentate gyrus, hippocampus) other than those traditionally thought to be involved in GH secretion (Bennett et al. 1997; Guan et al. 1997).

It would be desirable to know the molecular structure of growth hormone secretagogue receptors in order to analyze this new receptor family and understand its normal physiological role in: concert with the actions of GHRH and somatostatin. This could lead to a better understanding of the in vivo processes which occur upon ligand-receptor binding. Further, it would be desirable to use cloned-growth hormone secretagogue receptors as essential components of an assay system which can identify new growth hormone secretagogues which would confer a significant benefit on children and adults deficient in growth hormone, the frail elderly, those in post-hip fracture rehabilitation and post-operative recovery patients.

SUMMARY OF THE INVENTION

This invention relates to a novel receptor, mouse growth hormone secretagogue receptor (mGHS-R), which is free from receptor associated proteins. A further aspect of this invention is mGHS-R which is isolated or purified.

Another aspect of this invention is mGHS-Rs which are encoded by substantially the same nucleic acid sequence, but which have undergone changes in splicing or other RNA processing-derived modifications or mutagenesis induced changes, so that the expressed protein has a homologous, but different amino acid sequence from the native form. These variant forms may have different and/or additional functions in animal physiology or in vitro in cell based assays.

Growth hormone secretagogue receptors are proteins containing various functional domains, including one or more domains which anchor the receptor in the cell membrane, and at least one ligand binding domain. As with many receptor proteins, it is possible to modify many of the amino acids, particularly those which are not found in the ligand binding domain, and still retain at least a percentage of the biological activity of the original receptor. Thus, this invention specifically includes modified functionally equivalent mGHS-Rs which have deleted, truncated, or mutated N-terminal portions. This invention also specifically includes modified functionally equivalent mGHS-Rs which contain modified and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

A further aspect of this invention are nucleic acids which encode a mouse growth hormone secretagogue receptor or a functional equivalent. These nucleic acids may be free from associated nucleic acids, or they may be isolated or purified. For most cloning purposes, cDNA is a preferred nucleic acid, but this invention specifically includes other forms of DNA as well as RNAs which encode a mGHS-R or a functional equivalent.

Yet another aspect of this invention relates to vectors which comprise nucleic acids encoding mGHS-R or a functional equivalent. These vectors may be comprised of DNA or RNA; for most cloning purposes DNA vectors are preferred. Typical vectors include plasmids, modified viruses, bacteriophage and cosmids, yeast artificial chromosomes, transposable elements and other forms of episomal or integrated DNA that can encode a mGHS-R. It is well within the skill of the ordinary artisan to determine an appropriate vector for a particular gene transfer or other use.

A further aspect of this invention are host cells which are transformed with a vector comprising a gene which encodes a mouse growth hormone secretagogue receptor or a functional equivalent. The host cell may or may not naturally express a GHS-R on the cell membrane. Preferably, once transformed, the host cells are able to express the mouse growth hormone secretagogue receptor or a functional equivalent on the cell membrane. Depending on the host cell, it may be desirable to adapt the DNA so that particular codons are used in order to optimize expression. Such adaptations are known in the art, and these nucleic acids are also included within the scope of this invention. Generally, mammalian cell lines, such as COS, HEK-293, CHO, HeLa, NS/0, CV-1, GC, GH3 or VERO cells are preferred host cells, but other cells and cell lines such as Xenopus oocytes or insect cells, may also be used.

Another aspect of this invention is a process for identifying nucleic acids encoding mouse growth hormone secretagogue related receptors comprising hybridizing a first nucleic acid encoding a mouse growth hormone secretagogue receptor with a second nucleic acid suspected of comprising nucleic acids encoding a growth hormone secretagogue receptor, wherein the hybridizing takes place under relaxed or moderate post hybridizational washing conditions; and identify areas of the second nucleic acid where hybridization occurred.

BRIEF DESCRIPTION OF THE FIGURES

FIGS 1A–1B is the DNA sequence encoding the mouse GHS-R, 5' and 3' flanking regions and the intron; SEQ ID NO:1.

FIG. 2 is the DNA sequence encoding the open reading frame (ORF) of the mouse GHS-R; SEQ ID NO:2.

FIGS. 3A–3B is the deduced amino acid sequence of the mouse GHS-R; SEQ ID NO:3.

FIGS. 4A–4B is an amino acid alignment of the mouse GHS-R with other GHS-R's from several species (human—SEQ ID NO:4, rat—SEQ ID NO: 5, and swine—SEQ ID NO:6).

DETAILED DESCRIPTION OF THE INVENTION

As used throughout the specification and claims, the following definitions shall apply:

Growth Hormone Secretagogue—any compound or agent that directly or indirectly stimulates or increases the release of growth hormone in an animal.

Ligands—any molecule which binds to the mGHS-R of this invention. These ligands can have either agonist, partial agonist, partial antagonist or antagonist activity.

Free from receptor-associated proteins—the receptor protein is not in a mixture or solution with other membrane receptor proteins.

Free from associated nucleic acids—the nucleic acid is not covalently linked to DNA which it is naturally covalently linked in the organism's chromosome.

Isolated receptor—the protein is not in a mixture or solution with any other proteins.

Isolated nucleic acid—the nucleic acid is not in a mixture or solution with any other nucleic acid.

Functional equivalent—a receptor which does not have the exact same amino acid sequence of a naturally occurring mouse growth hormone secretagogue receptor due to alternative splicing, deletions, mutations, or additions, but retains at least 1%, preferably 10%, and more preferably 25% of the biological activity of the naturally occurring receptor. Such derivatives will have a significant homology with a natural mGHS-R and can be detected by reduced stringency hybridization with a DNA sequence obtained from a mGHS-R. The nucleic acid encoding a functional equivalent has at least about 50% homology at the nucleotide level to a naturally occurring receptor nucleic acid.

Purified receptor—the receptor is at least about 95% pure.

Purified nucleic acid—the nucleic acid is at least about 95% pure.

Standard or high stringency post hybridizational washing conditions—6×SSC at 55° C.

Moderate post hybridizational washing conditions—6× SSC at 45° C.

Relaxed post hybridizational washing conditions—6× SSC at 30° C.

The mouse isoform of the previously identified GHS-R was cloned from two genomic DNA libraries for the generation of a GHS-R knock-out mouse. This isoform has been shown to be functionally activated by secretagogues such as growth hormone releasing peptide GHRP-6 and MK-0677 through expression studies of the complete and contiguous open reading frame of mGHS-R using the aequorin biolumenescence assay. The proteins of this invention were found to have structural features which are typical of the 7-transmembrane domain (TM)-containing G-protein linked receptor superfamily (GPC-R's or 7-TM receptors), including seven transmembrane regions, three intra- and extracellular loops, and the GPC-R protein signature sequence. Thus, mGHS-R, as an additional member of the growth hormone secretagogue family of receptors, constitutes a new member of the GPC-R family of receptors. Note not all regions are required for functioning, and therefore this invention also comprises functional receptors which lack one or more non-essential domains.

Sequence analysis of the mGHS-R revealed, further, the presence of a non-coding, intronic sequence at nt 790 corresponding to a splice-donor site (G/GT) (FIG. 1). This sequence insertion occurs two amino acids after the completion of the predicted transmembrane domain (TM) 5 (leucine-263), thus dividing the ORF of the mouse GHS-R into an amino-terminal segment (encompassing the extracellular domain, TM-1 through TM-5, and the first two intra-and extra-cellular loops) and a carboxyl-terminal segment containing TM-6, TM-7, the third intra- and extracellular loops, and the intracellular domain. The point of insertion and flanking DNA sequence are highly conserved between human, swine, rat and mouse. Comparison of the complete ORF encoding the murine GHS-R type Ia protein sequence (FIG. 4) to rat, human and swine GHS-R homologs reveals a high degree of sequence identity (mouse vs. rat, 99.5%; mouse vs. human 95%; mouse vs. swine 94%).

The mGHS-Rs of this invention also share some sequence homology with previously cloned GPC-receptors including the rat and human neurotensin receptor (approximately 32% identity) and the rat and human thyrotropin releasing hormone (TRH) receptor (approximately 29% identity).

The mGHS-R and fragments are immunogenic. Thus, another aspect of this invention is antibodies and antibody fragments which can bind to mGHS-R or a mGHS-R fragment. These antibodies may be monoclonal antibodies and produced using either hybridoma technology or recombinant methods. They may be used as part of assay systems or to deduce the function of a mGHS-R present on a cell membrane.

A further aspect of this invention are antisense oligonucleotides—nucleotides which can bind to mGHS-R nucleotides and modulate receptor function or expression.

A further aspect of this invention is a method of increasing the amount of mGHS-Rs on a cell membrane comprising, introducing into the cell a nucleic acid encoding a mGHS-R, and allowing expression of the mGHS-R.

A mGHS receptor, preferably immobilized on a solid support, may be used diagnostically for the determination of the concentration of growth hormone secretagogues, or metabolites thereof, in physiological fluids, e.g. body fluids, including serum, and tissue extracts, as for example in patients who are undergoing therapy with a growth hormone secretagogue.

The administration of a mGHS receptor to a patient may also be employed for purposes of amplifying the net effect of a growth hormone secretagogue by providing increased downstream signaling following administration of the growth hormone secretagogue thereby diminishing the required dosage of growth hormone secretagogue; or diminishing the effect of an overdosage of a growth hormone secretagogue during therapy.

Yet a further aspect of the present invention is a method of identifying ligands comprising contacting the mGHS-R with a compound suspected of being a ligand specific for said receptor and determining whether binding occurs, binding constituting a positive indication of the presence of a ligand.

Ligands detected using assays described herein may be used in the treatment of conditions which occur when there is a shortage of growth hormone, such as observed in growth hormone deficient children, elderly patients with musculoskeletal impairment and those recovering from hip fracture, and osteoporosis.

Targeted disruption of the mouse GHS-R gene may also prove useful in elucidation of the mechanism of action and role of the growth hormone secretagogues in human and animal physiology.

The following, non-limiting Examples are presented to better illustrate the invention.

EXAMPLE 1

Isolation of Mouse GHS-R

A mouse (strain 129, liver) genotic library constructed in the vector lamda Fix II (Stratagene) was screened under moderate stringency hybridization conditions with a complete ORF probe derived from the swine GHS-R. Nylon filters repesenting $1.2 \times 10^6$ PFU were hybridized overnight at 58° C. in 6×SSC containing 10% dextran sulfate, 2% SDS, 0.5 M NaCl, and 100 µg/ml salmon sperm DNA with the random prime $^{32}$P-labeled swine GHS-R probe. Filters were washed in 4×SSC, 1% SDS at room temerature for 20 minutes, 4×SSC, 1% SDS at 55° C. for 30 min, 2×SSC, 1% SDS at 55° C. for 30 min, and 2×SSC, 1% SDS at 62° C. for 30 min. Three positive clones were identified, phage DNA was isolated, and partial DNA sequencing performed to verify that they encoded the murine GHS-R gene. In addition, a mouse genomic library constructed in a BAC vector and gridded in a filter array (Genome Systems, Inc) was screened under moderate stringency hybridization conditions as given above with a complete ORF probe dervived from the human GHS-R. A positive clone was identified from the BAC library.

EXAMPLE 2

Sequencing of Mouse GHS-R

The BAC clone was sequenced with ABI Prism BigDye terminator cycle sequencing ready reaction mix (P/N 4303149; PE Applied Biosystems, Foster City, Calif.) using 1 µg DNA/reaction, 5% DMSO, 100 ng primer—standard cycle sequencing. Reactions were run on an ABI Prism 377 DNA Sequencer with XL Upgrade (ABI Prism 377XL).

DNA from the positive lambda clones was prepared from a liquid lysate of the *E. coli* strain XLBlue MRA minus. For DNA sequencing, 500 ng of DNA was used under the same conditions as given above.

EXAMPLE 3

Analysis of Mouse GHS-R Sequence

Sequence analysis revealed the presence of a non-coding, intronic sequence at nt 790 corresponding to a splice-donor site (G/GT) (FIG. 1). This sequence insertion occurs two amino acids after the completion of the predicted transmembrane domain (TM) 5 (leucine-263), thus dividing the ORF of the mouse GHS-R into an amino-terminal segment (encompassing the extracellular domain, TM-1 through TM-5, and the first two intra-and- extra-cellular loops) and a carboxyl-terminal segment containing TM-6, TM-7, the third intra- and extra-cellular loops, and the intracellular domain. The point of insertion and flanking DNA sequence are highly conserved between human, swine, rat and:mouse. Comparison of the complete ORF encoding the murine GHS-R type Ia protein sequence (FIG. 4) to rat, human and swine GHS-R homologs reveals a high degree of sequence identity (mouse vs. rat, 99.5%; mouse vs. human 95%; mouse vs. swine 94%).

EXAMPLE 4

Construction of Mouse GHS-R Expression Plasmid

For expression studies in mammalian cells, a contiguous ORF (FIGS. 2 and 3) was assembled in the vector pcDNA-3 (Invitrogen) by overlapping PCR to remove the single intron present following nucleotide 790 of the ORF. To subclone, the Advantage HF PCR kit (K 1909-1; Clonetech Laboratories, Inc, Palo Alto, Calif.) was used under the following conditions: 94° C. for 1 min;, then 25 cycles of the following: 94° C. for 15 sec, 55° C. for 15 sec, and 68° C. for 3 min. The primers used were: primer 1-5'GGG CCC GAA TTC GCC GCC ATG TGG AAC GCG ACG CCC AGC 3' (SEQ ID NO:7, including EcoR I site, Kozak initation sequence, and translational start Met); primer 2-5'CAC CAC CAC AG C AAG CAT CTT CAC TGT CTG3' (SEQ ID NO:8; nucleotides shown in italic type overlap exon 2); primer 3-5'AAG ATG CTT G CT GTG GTG GTG TTT GCT TTC ATC3' (SEQ ID NO:9; nucleotides shown in italic type overlap exon 1); and primer 4-5'AGT TTA GCG GCC GCT CAT GTA TTG ATG CTC GAC TTT GT3' (SEQ ID NO:10, including Not I site and stop codon). "Overlapping" PCR was performed. The first PCR reactions were performed with primers 1 and 2 (exon 1) or 3 and 4 (exon 2). The second PCR reactions were performed with primers 1 and 4 (ORF). The second product was digested with EcoRI and NotI, agarose gel purified, ethanol precipitated, phenol extracted, and ligated into pcDNA3 with Ready-to-Go T4 Ligase (27-0361-01; Pharmacia, Piscataway, N.J.), and transformed into SCS1 cells (200231; Stratagene, La Jolla, Calif.). DNA was isolated with Wizard Plus miniprep (A1460; Promega, Madison, Wis.) and 500 ng was sequenced as above, but without DMSO.

EXAMPLE 5

Functional Activity of Mouse GHS-R

Measurement of mouse GHS-R expression in the aequorin-expressing stable reporter cell line 293-AEQ17 (Button et al., 1993 *Cell Calcium* 14:663–671.) was performed using a Luminoskan RT luminometer (Labsystems Inc., Gaithersburg, Md. 293-AEQ17 cells ($8 \times 10^5$ cells plated 18 hr. before transfection in a T75 flask) were transfected with 22 µg of pcDNA-3/mouse GHS-R plasmid DNA and 264 µg lipofectamine (Life Technologies). Forty hours after transfection, the apo-aequorin in the cells was charged for 1 hour with coelenterazine CP (10 µM) under reducing conditions (300 mM reduced glutathione) in ECB buffer (140 mM NaCl, 20 mM KCl, 20 mM HEPES-NaOH, pH=7.4, 5 mM glucose, 1 mM $MgCl_2$, 1 mM $CaCl_2$, 0.1 mg/ml bovine serum albumin). The cells were harvested, washed once in ECB medium and resuspended to 500,000 cells/ml. One hundred (100) µg of cell suspension (corresponding to $5 \times 10^4$ cells) was then injected into each well of a 96-well microtiter test plate, and the integrated light emission was recorded over 30 seconds, in 0.5 second units. Twenty (20) µl of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response. Data were analyzed using GraphPad Prism software V.2.0 (GraphPad Software, San Diego, Calif.).

What is claimed is:

1. An isolated mouse growth hormone secretagogue receptor (mGHS-R) comprising the amino acid sequence set forth in SEQ ID NO:3.

2. The mGHS-R according to claim 1 wherein said receptor is activated by a growth hormone secretagogue selected from the group consisting of releasing peptide GHRP-6 or MK-0677.

3. An isolated nucleic acid molecule comprising the nucleotide sequence set forth in SEQ ID NO:1.

4. The nucleic acid according to claim 3 which is DNA.

5. An isolated nucleic acid which encodes a mouse growth hormone secretagogue receptor comprising the amino acid sequence set forth in SEQ ID NO:3.

6. A vector comprising the isolated nucleic acid molecule according to claim 5.

7. A vector according to claim 6 which is selected from the group consisting of: plasmids, modified viruses, yeast artificial chromosomes, bacteriophages, cosmids and transposable elements.

8. A host cell comprising the vector according to claim 6.

9. A method of identifying ligands which comprises:
   (a) contacting the mGHS-R according to claim 2 with compounds suspected of being mGHS-R ligands; and
   (b) determining whether binding occurs, binding constituting a positive indication of the presence of a ligand.

10. An isolated nucleic acid molecule consisting of the nucleotide sequence set forth in SEQ ID NO:2 wherein said nucleotide sequence encodes a mGHS-R.

11. A vector comprising the nucleic acid molecule according to claim 10.

12. A host cell comprising the vector according to claim 11.

* * * * *

SEQUENCE LISTING

<160> NUMBER OF SEQ ID NOS: 10

<210> SEQ ID NO 1
<211> LENGTH: 4009
<212> TYPE: DNA
<213> ORGANISM: Mus musculus

<400> SEQUENCE: 1

| | | | | | |
|---|---|---|---|---|---|
| agagaggagc | cctcacacac | tcgctttgca | gcgcctgcct | tccgcaagag | cccacgcact | 60 |
| cggacgcttg | tggggagcac | gacaggcttg | ctggggcgag | atctccagtg | ccaggcaact | 120 |
| gctggtggcg | ccgccgtttg | agtgacaggt | aagtgagtgc | gtgacagtcg | aggctgtatt | 180 |
| gggagaccgg | gactgtgtgg | ggaagatagt | gggaaggggg | aagaaaagag | agatgtggga | 240 |
| gggaggggag | aggaggaacg | gaaggaaata | gggagagacg | tgcagtgggt | cactctcttc | 300 |
| ctttcatcgc | taatgttcgc | accccccattc | caccttctcc | taggcttctt | ctcacttctc | 360 |
| tcttccccaa | gcatccttcc | tgctgctcgc | gcccattcct | cccccacgc | cgcccccgc | 420 |
| ccggccccca | ctcttccgcg | cctaggagga | cctcctcagg | ggaccagatt | tccgcgcggc | 480 |
| tgcgacccca | agcctggcaa | catgtggaac | gcgacgccca | gcgaggagcc | ggagcctaac | 540 |
| gtcacgctgg | acctggactg | ggacgcttct | cccggcaacg | actcactctc | tgacgaactg | 600 |
| ctgccactgt | tccccgcgcc | gctgctggcg | ggcgtcactg | ccacctgcgt | ggcgctcttc | 660 |
| gtggtgggca | tctcgggcaa | cctgctcacc | atgctggtgg | tgtcccgctt | ccgcgagctg | 720 |
| cgcaccacca | ccaacctcta | cctatccagc | atggccttct | ccgatctgct | catcttcctg | 780 |
| tgcatgccgc | tggacctcgt | ccgcctctgg | cagtatcggc | cctggaactt | cggcgacctg | 840 |
| ctctgcaaac | tcttccagtt | tgtcagcgag | agctgcacct | acgccacggt | cctcaccatc | 900 |
| accgcgctga | gcgtcgagcg | ctacttcgcc | atctgcttcc | cgctgcgggc | caaggtggtg | 960 |
| gtcaccaagg | gccgtgtgaa | gctggtcatc | cttgtcatct | gggccgtggc | cttctgcagc | 1020 |
| gcggggccca | tcttcgtgct | ggtgggcgtg | agcacgaga | acggcacaga | tccccgggac | 1080 |
| accaacgagt | gccgcgccac | cgagttcgct | gtgcgctctg | ggctgctcac | cgtcatggtg | 1140 |
| tgggtgtcca | gcgtcttctt | ctttctaccg | gtcttctgcc | tcactgtgct | ctacagtctc | 1200 |
| atcgggagga | agctatggcg | gagacgcggc | gatgcagcgg | tgggcgcctc | gctccgggac | 1260 |
| cagaaccaca | aacagacagt | gaagatgctt | ggtgagttct | gacaccccgg | tggcttttct | 1320 |
| tccccactg | cttgctcttt | gccagagccc | tctatttctg | tttctggtcg | tctccatctc | 1380 |
| tccctaagtc | tctcaagtct | ctgtctgtct | ctgyctctct | sttggttctt | ggtctcactg | 1440 |
| ctttckggtt | ttttttcctc | tgtctgtccc | tgtatcttct | ccacgaaaaa | gcccctcata | 1500 |
| ttggcaattc | cctaaatgag | tactggtctg | ggaaatttgg | tccaagatgg | aaatacctca | 1560 |
| ttatggttta | ttgagtcccc | taattgttaa | yggtkymkcw | ymtwgwctca | catagaattt | 1620 |
| gtggttatcm | aagtmataat | attaaggtaa | gcaggcaggy | awtgggttta | gaaatyrctc | 1680 |
| catggtaart | ctaaccamaa | awttgggtca | ctctgttaar | gaygryttat | agatgtrttt | 1740 |
| tgtttgttttk | caatattrgg | atttrttytc | tgccctgcmy | ctkyctcaga | taattacatc | 1800 |
| cactcttgtt | tagtctatgg | ttttgccagg | aggggcttca | tgctgggtc | tcctttttct | 1860 |
| tgttttgta | tttgtctccc | cagtaatata | ggccaggata | gggtggagaa | gtcatccttt | 1920 |
| cctcaaactg | tccttcagga | aggtctgggt | actgaacggt | tactgcataa | actctgcttc | 1980 |
| cccaaaggca | tgtgcttggt | gtggtaaagt | catgaagatg | gtgctcatgt | ccaagaggaa | 2040 |

```
cctctgatct cacttttcaa gggatttcat gtttgctgac atttaatact tgttagtttt    2100
tgcaggggga tgatttctca tttgcaattt tattattctc aaattctgca tgtcagaatg    2160
ttagagattt ctcagggatg tcaggttctg tttccagatg agtgattgcc ctgtgtcctc    2220
cattggactg taaactcata tgcaccagac agggtctaca ttgctgccgt ggtgcatagc    2280
cttccatgtg tcacttagtc ctaaagagaa gttactaata acctaatctc actaatctca    2340
ctggcatctc aatgccgatc ccattgtcat ctgaaaattt gaaggggaca ttaaagtggc    2400
acagggacca gaacaatatt tttctctcat tgctgaattt taaaaacaat ctaaaaaatt    2460
ggaattcttg aagaaactat cttatatgac taaaatgaag ccttgggtgg gtgctaatta    2520
ttattgtctg gcttacctgc ccccccact  acttatatct tttagagatg acacagactt    2580
gctttccctg tggctactaa tcccaattgc acattcagtc ccttgataga cttactctaa    2640
aaatctaagt tcagcggtcc acgaaacata acaaagcctg tcctaaaaca gaaagaaaga    2700
aagaaagaaa gaaagaaaga agaaagaaaa gaaagaaaga agaaaacag  aagacaaaca    2760
aggtcttttcc ccattcccta acatacagga atggaaatta ttaagtctac gtgatagcca    2820
atgaatctgt ttcttaagta tgcccacaag ggtgctgccg gagccattgc tcagggctgg    2880
agtatttact gggcatgctt gaccccagca tggagggtga gaagtgctcc tgggaactct    2940
gatccactgc tgtggtggag agcaaacacc tggcctcatt tatacttgtt gtctgtataa    3000
tgcatataaa tggaggataa tcattaatga actgtttagt tgggtcatca tgccaagtca    3060
gtcacaaagc caagtcgtta tcacatagaa agactgggaa gcccagtgga gattgttagc    3120
tgttggtctg acagtctcac tgtgtgctat ctatagtgtt agaacggatg gaggcagtat    3180
ttatgtgaag agcagggtgt cgtgtttcct gtgtcaaaga gcaagatgtg atgtttgtca    3240
gtgggcatgc ccctcatgga gaaagagat  ccgggactta aaaatgtgaa gtgatttatg    3300
ccgtgtcaca cccatgctcc accctgatgg tctctctttg tgtgccttca gctgtggtgg    3360
tgtttgcttt catcctctgc tggctgccct tccacgtggg aagatatctg ttttccaagt    3420
cttttcgagcc tggctctctg gagatcgcgc agatcagtca gtactgcaac ctggtgtcct    3480
ttgtcctctt ctacctcagc gctgccatca accccattct gtacaacatc atgtccaaga    3540
agtaccgggt ggccgtgttc aaacttctag gatttgaatc cttctcccag agaaagcttt    3600
ccactctgaa ggatgagagt tcccgggcct ggacaaagtc gagcatcaat acatgacatc    3660
gcagcgcatc tctccgtcat cgctcattgc tccacaccag aagccatagc caagcgggac    3720
ttgggaggag gcagaacgtc agtttgggga ttagagacaa atggatctgg aaacaattgg    3780
gggtggggag tagagccaga tggcagggt  ccgtgcagat tgatctattt gtgcgcccac    3840
cagagcactc atgtgcagcc cctgcacacc tgtgtctgtg attttgcgaa tttgcatttg    3900
gagcttctga cagctttgca gctcgaagga gggaggggcg cagagcaggc aacggccgtc    3960
cttcttggtg tgtaacacta aactccattt gcttttctca tcataatag               4009
```

<210> SEQ ID NO 2
<211> LENGTH: 1095
<212> TYPE: DNA
<213> ORGANISM: Mus musculus

<400> SEQUENCE: 2

```
atgtggaacg cgacgcccag cgaggagccg gagcctaacg tcacgctgga cctggactgg      60
gacgcttctc ccggcaacga ctcactctct gacgaactgc tgccactgtt ccccgcgccg     120
```

```
ctgctggcgg gcgtcactgc cacctgcgtg gcgctcttcg tggtgggcat ctcgggcaac      180
ctgctcacca tgctggtggt gtcccgcttc cgcgagctgc gcaccaccac caacctctac      240
ctatccagca tggccttctc cgatctgctc atcttcctgt gcatgccgct ggacctcgtc      300
cgcctctggc agtatcggcc ctggaacttc ggcgacctgc tctgcaaact cttccagttt      360
gtcagcgaga gctgcaccta cgccacggtc ctcaccatca ccgcgctgag cgtcgagcgc      420
tacttcgcca tctgcttccc gctgcgggcc aaggtggtgg tcaccaaggg ccgtgtgaag      480
ctggtcatcc ttgtcatctg gccgtggcc ttctgcagcg cggggcccat cttcgtgctg       540
gtgggcgtgg agcacgagaa cggcacagat ccccgggaca ccaacgagtg ccgcgccacc      600
gagttcgctg tgcgctctgg gctgctcacc gtgatggtat gggtgtcgag cgtcttcttc      660
tttctgccgg tcttctgcct cactgtgctc tacagtctca tcgggaggaa gctgtggcgg      720
aggcgcggcg acgcggcggt gggctcctcg ctcagggacc agaaccacaa acagacagtg      780
aagatgcttg ctgtggtggt gtttgctttc atcctctgct ggctgcccct tccacgtggga     840 agatatctgt tttccaagtc tttcgagcct ggctctctgg agatcgcgca gatcagtcag      900
tactgcaacc tggtgtcctt tgtcctcttc tacctcagcg ctgccatcaa ccccattctc      960
tacaacatca tgtccaagaa gtaccgggtg gccgtgttca aacttctagg atttgaatcc     1020
ttctcccaga gaaagctttc cactctgaag gatgagagtt cccgggcctg gacaaagtcg     1080
agcatcaata catga                                                      1095
```

<210> SEQ ID NO 3
<211> LENGTH: 364
<212> TYPE: PRT
<213> ORGANISM: Mus musculus

<400> SEQUENCE: 3

```
Met Trp Asn Ala Thr Pro Ser Glu Glu Pro Glu Pro Asn Val Thr Leu
 1               5                  10                  15

Asp Leu Asp Trp Asp Ala Ser Pro Gly Asn Asp Ser Leu Ser Asp Glu
            20                  25                  30

Leu Leu Pro Leu Phe Pro Ala Pro Leu Leu Ala Gly Val Thr Ala Thr
        35                  40                  45

Cys Val Ala Leu Phe Val Val Gly Ile Ser Gly Asn Leu Leu Thr Met
    50                  55                  60

Leu Val Val Ser Arg Phe Arg Glu Leu Arg Thr Thr Thr Asn Leu Tyr
65                  70                  75                  80

Leu Ser Ser Met Ala Phe Ser Asp Leu Leu Ile Phe Leu Cys Met Pro
                85                  90                  95

Leu Asp Leu Val Arg Leu Trp Gln Tyr Arg Pro Trp Asn Phe Gly Asp
            100                 105                 110

Leu Leu Cys Lys Leu Phe Gln Phe Val Ser Glu Ser Cys Thr Tyr Ala
        115                 120                 125

Thr Val Leu Thr Ile Thr Ala Leu Ser Val Glu Arg Tyr Phe Ala Ile
    130                 135                 140

Cys Phe Pro Leu Arg Ala Lys Val Val Val Thr Lys Gly Arg Val Lys
145                 150                 155                 160

Leu Val Ile Leu Val Ile Trp Ala Val Ala Phe Cys Ser Ala Gly Pro
                165                 170                 175

Ile Phe Val Leu Val Gly Val Glu His Glu Asn Gly Thr Asp Pro Arg
            180                 185                 190

Asp Thr Asn Glu Cys Arg Ala Thr Glu Phe Ala Val Arg Ser Gly Leu
```

```
            195                 200                 205
Leu Thr Val Met Val Trp Val Ser Ser Val Phe Phe Leu Pro Val
            210                 215                 220
Phe Cys Leu Thr Val Leu Tyr Ser Leu Ile Gly Arg Lys Leu Trp Arg
225                 230                 235                 240
Arg Arg Gly Asp Ala Ala Val Gly Ser Ser Leu Arg Asp Gln Asn His
                245                 250                 255
Lys Gln Thr Val Lys Met Leu Ala Val Val Phe Ala Phe Ile Leu
            260                 265                 270
Cys Trp Leu Pro Phe His Val Gly Arg Tyr Leu Phe Ser Lys Ser Phe
                275                 280                 285
Glu Pro Gly Ser Leu Glu Ile Ala Gln Ile Ser Gln Tyr Cys Asn Leu
290                 295                 300
Val Ser Phe Val Leu Phe Tyr Leu Ser Ala Ala Ile Asn Pro Ile Leu
305                 310                 315                 320
Tyr Asn Ile Met Ser Lys Lys Tyr Arg Val Ala Val Phe Lys Leu Leu
                325                 330                 335
Gly Phe Glu Ser Phe Ser Gln Arg Lys Leu Ser Thr Leu Lys Asp Glu
                340                 345                 350
Ser Ser Arg Ala Trp Thr Lys Ser Ser Ile Asn Thr
                355                 360

<210> SEQ ID NO 4
<211> LENGTH: 366
<212> TYPE: PRT
<213> ORGANISM: Homo sapiens

<400> SEQUENCE: 4

Met Trp Asn Ala Thr Pro Ser Glu Glu Pro Gly Phe Asn Leu Thr Leu
1               5                   10                  15
Ala Asp Leu Asp Trp Asp Ala Ser Pro Gly Asn Asp Ser Leu Gly Asp
                20                  25                  30
Glu Leu Leu Gln Leu Phe Pro Ala Pro Leu Leu Ala Gly Val Thr Ala
                35                  40                  45
Thr Cys Val Ala Leu Phe Val Val Gly Ile Ala Gly Asn Leu Leu Thr
50                  55                  60
Met Leu Val Val Ser Arg Phe Arg Glu Leu Arg Thr Thr Thr Asn Leu
65                  70                  75                  80
Tyr Leu Ser Ser Met Ala Phe Ser Asp Leu Leu Ile Phe Leu Cys Met
                85                  90                  95
Pro Leu Asp Leu Val Arg Leu Trp Gln Tyr Arg Pro Trp Asn Phe Gly
                100                 105                 110
Asp Leu Leu Cys Lys Leu Phe Gln Phe Val Ser Glu Ser Cys Thr Tyr
                115                 120                 125
Ala Thr Val Leu Thr Ile Thr Ala Leu Ser Val Glu Arg Tyr Phe Ala
                130                 135                 140
Ile Cys Phe Pro Leu Arg Ala Lys Val Val Val Thr Lys Gly Arg Val
145                 150                 155                 160
Lys Leu Val Ile Phe Val Ile Trp Ala Val Ala Phe Cys Ser Ala Gly
                165                 170                 175
Pro Ile Phe Val Leu Val Gly Val Glu His Glu Asn Gly Thr Asp Pro
                180                 185                 190
Trp Asp Thr Asn Glu Cys Arg Pro Thr Glu Phe Ala Val Arg Ser Gly
                195                 200                 205
```

```
Leu Leu Thr Val Met Val Trp Val Ser Ser Ile Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Phe Ala Phe
            260                 265                 270

Ile Leu Cys Trp Leu Pro Phe His Val Gly Arg Tyr Leu Phe Ser Lys
        275                 280                 285

Ser Phe Glu Pro Gly Ser Leu Glu Ile Ala Gln Ile Ser Gln Tyr Cys
    290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
            355                 360                 365

<210> SEQ ID NO 5
<211> LENGTH: 364
<212> TYPE: PRT
<213> ORGANISM: Rattus norvegicus

<400> SEQUENCE: 5

Met Trp Asn Ala Thr Pro Ser Glu Glu Pro Glu Pro Asn Val Thr Leu
1               5                   10                  15

Asp Leu Asp Trp Asp Ala Ser Pro Gly Asn Asp Ser Leu Pro Asp Glu
            20                  25                  30

Leu Leu Pro Leu Phe Pro Ala Pro Leu Leu Ala Gly Val Thr Ala Thr
        35                  40                  45

Cys Val Ala Leu Phe Val Val Gly Ile Ser Gly Asn Leu Leu Thr Met
    50                  55                  60

Leu Val Val Ser Arg Phe Arg Glu Leu Arg Thr Thr Thr Asn Leu Tyr
65                  70                  75                  80

Leu Ser Ser Met Ala Phe Ser Asp Leu Leu Ile Phe Leu Cys Met Pro
                85                  90                  95

Leu Asp Leu Val Arg Leu Trp Gln Tyr Arg Pro Trp Asn Phe Gly Asp
            100                 105                 110

Leu Leu Cys Lys Leu Phe Gln Phe Val Ser Glu Ser Cys Thr Tyr Ala
        115                 120                 125

Thr Val Leu Thr Ile Thr Ala Leu Ser Val Glu Arg Tyr Phe Ala Ile
    130                 135                 140

Cys Phe Pro Leu Arg Ala Lys Val Val Thr Lys Gly Arg Val Lys
145                 150                 155                 160

Leu Val Ile Leu Val Ile Trp Ala Val Ala Phe Cys Ser Ala Gly Pro
                165                 170                 175

Ile Phe Val Leu Val Gly Val Glu His Glu Asn Gly Thr Asp Pro Arg
            180                 185                 190

Asp Thr Asn Glu Cys Arg Ala Thr Glu Phe Ala Val Arg Ser Gly Leu
        195                 200                 205

Leu Thr Val Met Val Trp Val Ser Ser Val Phe Phe Leu Pro Val
    210                 215                 220
```

```
Phe Cys Leu Thr Val Leu Tyr Ser Leu Ile Gly Arg Lys Leu Trp Arg
225                 230                 235                 240

Arg Arg Gly Asp Ala Ala Val Gly Ala Ser Leu Arg Asp Gln Asn His
            245                 250                 255

Lys Gln Thr Val Lys Met Leu Ala Val Val Phe Ala Phe Ile Leu
        260                 265                 270

Cys Trp Leu Pro Phe His Val Gly Arg Tyr Leu Phe Ser Lys Ser Phe
            275                 280                 285

Glu Pro Gly Ser Leu Glu Ile Ala Gln Ile Ser Gln Tyr Cys Asn Leu
            290                 295                 300

Val Ser Phe Val Leu Phe Tyr Leu Ser Ala Ala Ile Asn Pro Ile Leu
305                 310                 315                 320

Tyr Asn Ile Met Ser Lys Lys Tyr Arg Val Ala Val Phe Lys Leu Leu
                325                 330                 335

Gly Phe Glu Ser Phe Ser Gln Arg Lys Leu Ser Thr Leu Lys Asp Glu
            340                 345                 350

Ser Ser Arg Ala Trp Thr Lys Ser Ser Ile Asn Thr
            355                 360

<210> SEQ ID NO 6
<211> LENGTH: 366
<212> TYPE: PRT
<213> ORGANISM: Sus scrofa

<400> SEQUENCE: 6

Met Trp Asn Ala Thr Pro Ser Glu Glu Pro Gly Pro Asn Leu Thr Leu
1               5                   10                  15

Pro Asp Leu Gly Trp Asp Ala Pro Pro Glu Asn Asp Ser Leu Val Glu
            20                  25                  30

Glu Leu Leu Pro Leu Phe Pro Thr Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Met Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Phe Arg Leu Trp Gln Tyr Arg Pro Trp Asn Leu Gly
            100                 105                 110

Asn Leu Leu Cys Lys Leu Phe Gln Phe Val Ser Glu Ser Cys Thr Tyr
            115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Val Thr Lys Gly Arg Val
145                 150                 155                 160

Lys Leu Val Ile Leu Val Ile Trp Ala Val Ala Phe Cys Ser Ala Gly
                165                 170                 175

Pro Ile Phe Val Leu Val Gly Val Glu His Asp Asn Gly Thr Asp Pro
            180                 185                 190

Arg Asp Thr Asn Glu Cys Arg Ala Thr Glu Phe Ala Val Arg Ser Gly
            195                 200                 205

Leu Leu Thr Val Met Val Trp Val Ser Ser Val Phe Phe Leu Pro
    210                 215                 220

Val Phe Cys Leu Thr Val Leu Tyr Ser Leu Ile Gly Arg Lys Leu Trp
```

-continued

```
                            225                 230                 235                     240
        Arg Arg Lys Arg Gly Glu Ala Ala Val Gly Ser Ser Leu Arg Asp Gln
                        245                 250                 255

Asn His Lys Gln Thr Val Lys Met Leu Ala Val Val Phe Ala Phe
                    260                 265                 270

Ile Leu Cys Trp Leu Pro Phe His Val Gly Arg Tyr Leu Phe Ser Lys
                    275                 280                 285

Ser Leu Glu Pro Gly Ser Val Glu Ile Ala Gln Ile Ser Gln Tyr Cys
                290                 295                 300

Asn Leu Val Ser Phe Val Leu Phe Tyr Leu Ser Ala Ala Ile Asn Pro
        305                 310                 315                 320

Ile Leu Tyr Asn Ile Met Ser Lys Lys Tyr Arg Val Ala Val Phe Lys
                        325                 330                 335

Leu Leu Gly Phe Glu Pro Phe Ser Gln Arg Lys Leu Ser Thr Leu Lys
                        340                 345                 350

Asp Glu Ser Ser Arg Ala Trp Thr Glu Ser Ser Ile Asn Thr
                    355                 360                 365

<210> SEQ ID NO 7
<211> LENGTH: 39
<212> TYPE: DNA
<213> ORGANISM: PCR primer

<400> SEQUENCE: 7
gggcccgaat tcgccgccat gtggaacgcg acgcccagc                                    39

<210> SEQ ID NO 8
<211> LENGTH: 30
<212> TYPE: DNA
<213> ORGANISM: PCR primer

<400> SEQUENCE: 8
caccaccaca gcaagcatct tcactgtctg                                              30

<210> SEQ ID NO 9
<211> LENGTH: 33
<212> TYPE: DNA
<213> ORGANISM: PCR primer

<400> SEQUENCE: 9
aagatgcttg ctgtggtggt gtttgctttc atc                                          33

<210> SEQ ID NO 10
<211> LENGTH: 38
<212> TYPE: DNA
<213> ORGANISM: PCR primer

<400> SEQUENCE: 10
agtttagcgg ccgctcatgt attgatgctc gactttgt                                     38
```